United States Patent [19]

Hibbel et al.

[11] 4,242,283

[45] Dec. 30, 1980

[54] PROCESS FOR CONTINUOUSLY PRODUCING OXYGEN-CONTAINING COMPOUNDS

[75] Inventors: Josef Hibbel; Gunther Kessen; Josef Meis, all of Oberhausen, Fed. Rep. of Germany

[73] Assignee: Ruhrchemie Aktiengesellschaft, Oberhausen, Fed. Rep. of Germany

[21] Appl. No.: 953,226

[22] Filed: Oct. 13, 1978

[30] Foreign Application Priority Data

Oct. 21, 1977 [DE] Fed. Rep. of Germany ....... 2747302

[51] Int. Cl.$^3$ ...................... C07C 45/50; C07C 27/20
[52] U.S. Cl. ..................................... 568/451; 568/909
[58] Field of Search .................. 260/604 HF; 568/909

[56] References Cited

U.S. PATENT DOCUMENTS 2,557,701  6/1951  Smith ........................... 260/604 HF
3,929,900  12/1975  Schnur et al. ................. 260/604 HF

FOREIGN PATENT DOCUMENTS 2263498  12/1972  Fed. Rep. of Germany .... 260/604 HF
2538037   4/1977  Fed. Rep. of Germany .... 260/604 HF

*Primary Examiner*—Werren B. Lone
*Attorney, Agent, or Firm*—Sprung, Felfe, Horn, Lynch & Kramer

[57] ABSTRACT

An improved process for continuously producing oxygen-containing compounds by the oxo process from olefins, carbon monoxide and hydrogen at a pressure of 5 to 1000 bar and at a temperature of 50° to 200° C. in the presence of a metal of Group VIII and/or a compound thereof as catalyst is disclosed. According to the invention, the unreacted olefin carbon monoxide and hydrogen is passed to a high pressure reactor wherein unreacted olefin is reacted under oxo process conditions to form oxygen-containing compounds.

9 Claims, No Drawings

PROCESS FOR CONTINUOUSLY PRODUCING OXYGEN-CONTAINING COMPOUNDS

BACKGROUND OF THE INVENTION

1. Field of the Invention

The present invention relates to a process for the production of oxygen-containing compounds by the oxo process by reacting olefinic hydrocarbons with carbon monoxide and hydrogen, said process permitting an improved conversion of the starting materials.

2. Discussion of the Prior Art

The oxo synthesis or hydroformylation is conventionally carried out in a high pressure tubular reactor as a liquid phase process. The liquid phase consists of the oxo product and olefin dissolved therein. Olefin, synthesis gas and a suitable metal compound such as compounds of cobalt or rhodium in solution or suspension are added in controlled amounts at the base of the reactor. In the reactor which is operated within wide ranges of pressure and temperature, e.g. at about 5 to 1000 bar and 50° to 200° C., e.g. with the use of cobalt as the catalyst at 200 to 300 bar and 130° to 180° C., the corresponding carbonyl or hydrocarbonyl which catalyzes the hydroformylation is formed from the metal compound. The reaction product which is a mixture of oxygen-containing compounds and unreacted starting materials leaves the reactor at the top and is cooled in a downstream of the reactor to a temperature at which reaction no longer takes place. Thereafter, the mixture is fed to a high pressure separator in which the separator into the liquid phase and gaseous phase takes place. In addition, it is the purpose of the gas separator to ensure that the reaction product flows uniformly from the reactor system. The gas leaving at the top of the separator may be admixed with the fresh gas and reintroduced to the reactor. The liquid phase is withdrawn at the base of the separator and thereafter depressurized into a catalyst decomposition vessel. The liquid level in the gas separator is maintained constant by appropriate control apparatus.

Various process for converting the olefin charged to the oxo synthesis as far as possible into the desired reaction products have been proposed.

According to the disclosure of German Pat. No. 935,126, the oxygen-containing compounds obtained in the first reaction stage are separated from the unreacted reaction mixture and then at least part of this mixture containing an unsaturated olefinic compound is reacted with carbon monoxide and hydrogen in at least one subsequent reaction stage to form oxygen-containing organic compounds.

In the process disclosed in U.S. Pat. No. 2,557,701, maximum conversion of olefin is achieved by returning the oxo raw product under the oxo reaction pressure from the high pressure separator to the reactor and readily mixing the gas and liquid streams in a controlled manner by subdividing the reactor in separate chambers.

In the variant of the process described in German Offenlegungsschrift (DE-OS) No. 2,263,498, the reaction is carried out in a reactor consisting of two or three chambers which are series-connected in such a manner that the gas and liquid streams are passed in a predetermined direction. Olefin conversions of more than 99% can be obtained by this measure.

A two-stage process for hydroformylating olefins is disclosed in German Offenlegungsschrift (DE-OS) No. 25 38 037. In this process, the hydroformylation is carried out in a first stage to a conversion of 40 to 75% depending upon the reaction mixture and then, in a second stage, to a conversion of at least 95% and preferably 95 to 98% without backmixing.

All of the processes mentioned above suffer from the disadvantage that they require high apparative outlay. Either special reactor designs are necessary or additional process steps must be included.

On the other hand, an attempt to increase the olefin conversion by high amounts of catalyst or increase in reaction temperatures results in increased information of undesirable higher boiling compounds. In addition, hydroformylation of propylene under these conditions results to an increased extent in iso compounds which can hardly be commerically utilized.

Accordingly, it is an object of the present invention to provide a process which permits olefin conversions of more than 99% to be achieved with additional process steps and with the use of reactors of as simple a design as possible.

In addition, it is an object of the invention to provide a process capable of being used not only in new plants but also in existing plants which are already in operation without their being extensively rebuilt.

SUMMARY OF THE INVENTION

Broadly, this invention contemplates an improvement in the process for continuously producing an oxygen-containing compound by the oxo process from olefins, carbon monoxide and hydrogen at a pressure of 5 to 1000 bar and at a temperature of 50° to 200° C. in the presence of a Group VIII metal or a compound thereof employed as catalyst wherein the reaction product leaving the reactor and containing unreacted olefin, carbon monoxide and hydrogen is past into a high pressure gas separator, the improvement comprising reacting unreacted olefin (which has not been reacted in the reactor) in the high pressure gas separator under oxo process reaction conditions such as the typical reaction conditions prevailing in a reactor whereby to form additional oxygen-containing compounds.

The process of the invention can be conducted by cooling the reaction mixture from the reactor enroute to the high pressure gas separator. Broadly speaking, the reaction conditions in the high pressure gas separator are those generally applicable for the reactor itself and include pressures of 5 to 1000 bar at temperatures of 50° to 200° C.

The reaction of starting materials which are still present (for example, when hydroformylating propylene, the reaction mixture still contains about 3 to 5% of unreacted olefin) in the high pressure gas separator is achieved in a simple manner by cooling the reaction product having left the reactor to not less than 120° C., when hydroformylating propylene in the presence of a cobalt catalyst. Cooling may be effected in a separate cooler downstream of the reactor or by means of a cooler arranged in the high pressure separator.

In conventional single-compartment oxo reactor, i.e. reactors which do not exhibit special chambers for the guidance of the product, the olefin conversion with economically justifiable consumption of catalyst can hardly be increased beyond about 97% even in case of highly reactive olefins of low carbon number. Surprisingly, one can, by operating the high pressure gas separator arranged downstream of the reactor at the reaction temperature, increase the olefin conversion to 99% and more without impairing the product composition. Due to the low olefin concentration in the reaction product leaving the reactor, a post-reaction proceeding at a high rate in the high pressure gas separator and resulting in valuable products could not be expected. One would have assumed that the reaction of the residual olefin, in a similar manner as in the reactor, would take place at a lower rate and that an undesirably high proportion of the primary aldehyde products would have been converted into secondary products, especially thick oil.

The temperature in the high pressure gas separator is adjusted to about the same level as in the reactor. It is dependent upon the type of olefin charged and the catalyst used and ranges, for example, between 135° and 155° C., and preferably between 140° and 150° C. when hydroformylating propylene and between 155° and 175° C. when hydroformylating diisobutylene. As has been mentioned above, the necessary reaction temperatures, above all in plants which are already in operation, are achieved most conveniently by cooling the reaction product leaving the reactor just as far that the desired reaction temperature establishes itself in the separator due to the heat released by the reaction.

The residence time of the reactants in the high pressure gas separator is adjusted by means of the liquid level to between 3 and 30 minutes, depending upon the reaction rate of the particular olefin. When hydroformylating propylene, a residence time in the range 3 to 8 minutes has been found to be favorable.

The rate of conversion in the high pressure separator may be influenced by varying the residence time and/or temperature.

When hydroformylating propylene, a total conversion in the reactor and in the separator between 99.2 and 99.5% has been found to be optimum. With total conversions in this range, a difference between the reaction products leaving the reactor and those leaving the high pressure gas separator can hardly be found.

On the other hand, still higher rates of conversion (in excess of 99.5% in case of propylene) result in considerably increased formation of secondary products such as butanol, butyl formate and undesirable higher boiling products. The fact that this undesirable preferential formation of higher boiling products in the high pressure gas separator exceeds the additional recovery of useful products when closely approaching 100% the conversion could hardly have been predicted.

The rate of conversion of olefins in the reactor having a higher carbon number than propylene is lower than that of propylene. Therefore, the conversion of these higher olefins can be increased in the high pressure gas separator to a considerably higher degree than in the case of propylene.

It is one particular advantage of the new process that the reaction between olefin and carbon monoxide and hydrogen is carried out in steps in such a manner that the maximum conversions achievable in the reactor is not sought but one is satisfied with a lower conversion in the reactor so that the reaction can be completed in the high pressure separator. This mode of operation has the advantage that the proportion of less valuable higher boiling products is reduced in favor of the desired valuable products. In addition, the consumption of catalyst is markedly reduced.

In order to more fully illustrate the invention and the manner of practicing the same, the following examples are presented.

EXAMPLE 1: Without conversion of residual olefin; prior art mode of operation 5.46 Tons per hour of a propylene/propane mixture containing 95.0% of propylene were charged to an oxo reactor of known construction having a reaction volume of 10.3 cu.m. and equipped with a cooler. The consumption of synthesis gas containing 99.8% of carbon monoxide and hydrogen in a ratio by volume of 1.0:1.0 was 6,880 standard cubic meters per hour. The temperature of the reactor ranged between 142° and 144° C. The reactor pressure was 280 bar.

The oxo raw product leaving the reactor at the top was introduced into the top of the high pressure gas separator together with unreacted synthesis gas after having been cooled to 100° C. The high pressure gas separator had a diameter of 450 mm. and a length of 9.0 m. After a residence time of 5 minutes, the oxo raw product, freed from undissolved gas, was withdrawn from the separator at the bottom by means of a level control valve.

With a propylene conversion of 97.0%, the oxo raw product, freed from cobalt, consisted of the following products based on 100 kg. of 100% propylene charged:
109.3 kg. of n-butyraldehyde
11.0 kg. of n-butanol and n-butyl formate
29.3 kg. of isobutyraldehyde
5.2 kg. of isobutanol and isobutylformate
10.0 kg. of higher boiling products (thick oil)
1.3 kg. of propylene were hydrogenated to propane.

EXAMPLE 2: With conversion of residual olefin; mode of operation according to the invention The same amount of propylene and catalyst was charged to the oxo reactor described in Example 1 under the same conditions. With the same amount of recycle gas as described in Example 1, 7, 100 standard cubic meters per hour of synthesis gas were needed. The oxo raw product-synthesis gas mixture was cooled to 120° C. and introduced into the high pressure gas separator 1 m. below the top of the latter. The reaction mixture in the high pressure gas separator had a temperature of 145° C. due to the residual conversion. The level of 50% permits a residence time of 5 minutes. The oxo raw product leaving at the base was cooled to 100° C. and depressurized into the cayalyst decomposition vessel.

The propylene conversion was 97.0% downstream of the reactor and 99.2% downstream of the gas separator. The oxo raw product contained the following constituents based on 100 kgs. of 100% porpylene charged:
111.0 kg. of n-butyraldehyde
11.3 kg. of n-butanol and n-butyl formate
30.1 kg. isobutryraldehyde
15.4 kg. of isobutanol and isobutyl formate
10.4 kg. of higher boiling products (thick oil)
1.4 kg. of propylene had been hydrogenated to propane.

EXAMPLE 3: Mode of operation as in Example 2

The amount of propylene charged was the same as that in Example 1. The requirement of synthesis gas was 7,050 standard cubic meters per hour under otherwise identical conditions.

In the high pressure gas separator, the reaction temperature was increased to 150° C. and the residence time to 6 minutes.

The propylene conversion was 96.3% downstream of the reactor and 99.0% downstream of the gas separator. The oxo raw product contained per 100 kg. of 100% propylene charged 112.0 kg. of n-butylraldehyde
11.0 kg. of n-butanol and n-butyl formate
30.5 kg. of isobutyraldehyde
5.2 kg. of isobutanol and isobutyl formate
9.3 kg. of higher boiling products (thick oil)
1.3 kg. of propylene were hydrogenated to form propane.

What is claimed is:

1. In a process for continuously producing an aldehyde or alcohol by the oxo process by contacting an olefin, carbon monoxide and hydrogen at a pressure of 5 to 1000 bar and at a temperature of 50° to 200° C. in the presence of a Group VIII metal or a compound thereof as catalyst wherein the reaction product so formed comprising unreacted olefin, carbon monoxide and hydrogen is passed to a high pressure gas separator the improvement wherein olefin which has not been reacted in the reactor is reacted in the high pressure gas separator under oxo process conditions comprising a pressure of 5 to 1000 bars and a temperature of 50° C. to 200° C. to form an aldehyde or alcohol.

2. A process according to claim 1 wherein the residence time of the reactants in the high pressure gas separator is 3 to 30 minutes, the temperature is 120° to 175° C. and the catalyst is a cobalt catalyst.

3. A process according to claim 2 wherein the residence time of the reactants in the high pressure gas separator is 5 to 15 minutes.

4. A process according to claim 1 wherein the olefin is propylene.

5. A process according to claim 1 wherein the temperature of the reaction mixture in the high pressure gas separator is between 135° and 155° C.

6. A process according to claim 1 wherein the temperatures of the reaction mixture is between 140° and 150° C. and propylene is the olefin.

7. A process according to claim 1 wherein the temperature of the reaction mixture and high pressure gas separator is between 155° and 175° C. and diisobutylene is the olefin.

8. A process according to claim 5 wherein the olefin is propylene and the same has a residence time in the high pressure gas separator of 3 to 8 minutes.

9. A process according to claim 1 wherein the unreacted olefin is reacted in the high pressure gas separator under reaction conditions prevailing in the reactor.

* * * * *